US009151730B2

(12) United States Patent
Lee

(10) Patent No.: US 9,151,730 B2
(45) Date of Patent: Oct. 6, 2015

(54) METHOD FOR DETERMINING THE ELECTROCHEMICAL CHARACTERISTIC OF A TEST STRIP

(71) Applicant: Joinsoon Medical Technology Co., Ltd., Taipei County (TW)

(72) Inventor: Jen Fang Lee, Taipei County (TW)

(73) Assignee: Joinsoon Medical Technology Co., Ltd., New Taipei (TW)

( * ) Notice: Subject to any disclaimer, the term of this patent is extended or adjusted under 35 U.S.C. 154(b) by 389 days.

(21) Appl. No.: 13/675,932

(22) Filed: Nov. 13, 2012

(65) Prior Publication Data

US 2013/0118919 A1 May 16, 2013

(30) Foreign Application Priority Data

Nov. 14, 2011 (TW) .............................. 100141396 A

(51) Int. Cl.
*G01N 27/327* (2006.01)
*G01N 27/416* (2006.01)

(52) U.S. Cl.
CPC ........ *G01N 27/4163* (2013.01); *G01N 27/3274* (2013.01)

(58) Field of Classification Search
CPC ......... G01N 27/327–27/3274; G01N 27/4163; C12Q 1/00–1/006
See application file for complete search history.

(56) References Cited

U.S. PATENT DOCUMENTS

2005/0161345 A1* 7/2005 Groll et al. .................... 205/792
2009/0014339 A1* 1/2009 Beer et al. ................... 205/777.5

* cited by examiner

*Primary Examiner* — J. Christopher Ball
(74) *Attorney, Agent, or Firm* — Novak Druce Connolly Bove + Quigg LLP

(57) ABSTRACT

This invention relates to a non-destructive means to determine electrochemical characteristics in biosensor test strips, including first applying a cyclic oxidative and reductive electric potential onto the inspection pads connecting to the reference electrode and working electrode, on which lies a drop of enzyme reagent solution, to homogenize the electrochemical characteristics of the biosensor test strips, and then applying an inspection electric potential within a short period of time over the inspection pads connecting to the reference electrode and working electrode to measure its electrical resistance to identify any abnormal biosensor test strips if present. Afterwards, embodiments of the present invention applies a reverse electric potential, having the same time interval as the inspection electric potential, onto the inspection pads connecting to the reference electrode and working electrode to prevent degradation on mediators such as potassium ferricyanide.

18 Claims, 5 Drawing Sheets

METHOD FOR DETERMINING THE ELECTROCHEMICAL CHARACTERISTIC OF A TEST STRIP

CROSS-REFERENCE TO RELATED APPLICATION

This application claims the priority benefit of Taiwan application serial no. 100141396, filed on Nov. 14, 2011, the entire content of which is hereby incorporated by reference.

BACKGROUND OF THE INVENTION

1. Field of the Invention

The present invention relates generally to an electrochemical biosensor and, more particularly, to a method for determining the electrochemical characteristics associated with a biosensor test strip.

2. Description of the Related Art

Diabetic patients routinely use over-the-counter blood glucose meters to measure their blood glucose levels. First, the patient inserts a blood glucose test strip into its associated blood glucose meter. Then, the patient places a drop of blood sample over the test strip, causing the blood sample to react with an enzyme reagent, which is placed on the reaction zone over the working electrode and the reference electrode. At this time, by applying a fixed or variable electric potential across the reaction zone, the blood glucose meter may calculate the blood glucose level based on the electrochemical characteristics generated from the measured voltage or current.

The accuracy of the blood glucose reading, however, depends on several factors, some of which are difficult to control. For example, the accuracy depends on the materials used in the test strips. In particular, the accuracy depends on the surface properties of the working and the reference electrodes, which tend to vary among individual test strips. Moreover, some electrochemical characteristics of the enzyme reagents are highly susceptible to manufacturing and environmental variables. These variables may negatively affect, for example, the number and sizes of the air bubbles present in the enzyme reagent and hence the homogeneous distribution of the enzyme and mediator, such as potassium ferricyanide. These variables may also negatively affect the coverage completeness of the enzyme reagent over the reaction zone. All of these may cause significant differences in the performance among test strips under the same testing conditions. Accounting for, but not limited to, the above problems, manufacturers often assign batch-specific codes to the test strips to account for the variability among each batch. This practice, however, increases the production cost and makes the glucose monitoring system less user-friendly.

Since physicians often refer to blood glucose readings as an aid to monitor the effectiveness of diabetes management and to give appropriate medical treatments, the accuracy of the readings is very critical. Accordingly, at the end of the manufacturing processes of the test strips, usually a number of test strips are randomly selected from a manufacturing batch to test for their conformity with the specification. This sampling method, however, cannot guarantee the quality of the entire batch of test strips, and cannot remove the defective test strips, if present, in the batch. Moreover, because the quality assurance test conducted on a selected test strip is usually destructive and non-reversible, the selected test strip loses its value after the test. This in turn increases the cost of sampling, and limits the number of test strips available for sale. Therefore, there is a need in the art to provide an accurate and non-destructive method to assure the quality of a biosensor test strip.

SUMMARY OF THE INVENTION

An objective of the present invention is to provide an accurate and non-destructive method to assure the quality of a biosensor test strip in the manufacturing processes.

According to one embodiment of the present invention, the surface characteristic of a test strip is first homogenized by a homogenizing process (cyclic electric potential). Then, a quality assurance test with an inspection electric potential is conducted on the test strip during the manufacturing process after dispensing the enzyme reagent solution, but before the enzyme reagent is dried, to determine if a defective test strip is present, which may be marked and then removed. Finally, the test strip is subject to a reverse electric potential adapted to substantially restore the test strip back to its original condition before testing in the manufacturing processes.

According to another embodiment of the present invention, the homogenizing process comprises applying to the enzyme reagent a cyclic oxidative and reductive electric potential adapted to homogenize the electrochemical characteristic on the surface of the test strip. Afterwards, an inspection electric potential is applied to the enzyme reagent to determine the homogenized electrochemical performance. Finally, a reverse electric potential is applied to the enzyme reagent to prevent the mediator, such as potassium ferricyanide, in the enzyme reagent from degradation.

BRIEF DESCRIPTION OF THE DRAWINGS

The described embodiments of the present invention will be apparent through examination of the following detailed description in conjunction with the accompanying drawings, in which.

DETAILED DESCRIPTION OF THE INVENTION

Figure 1:
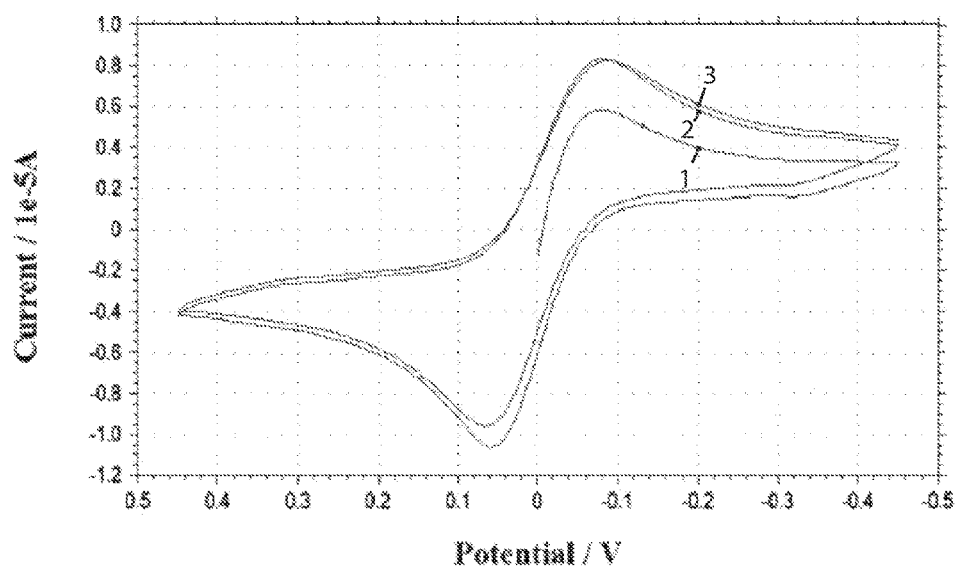
FIG. 1 is a diagram of voltage-current relationship, illustrating a cyclic oxidative and reductive electric potential according to an embodiment of the present invention.

To be consistent throughout the descriptions and for clear understanding of the present invention, the following definitions are hereby provided for terms used therein:

The term "biosensor" refers to an analytical device, or an analytical device system, for the detection of biologically or chemically related substances or properties. For example, a blood glucose biosensor (or sometimes a blood glucose meter), may use an enzyme reagent to determine the blood glucose level.

The term "test strip" may refer to a device used in conjuncture with a biosensor or a component of a biosensor. A test strip may be a single-use test strip or a multi-use test strip. For example, in blood glucose testing, a single-use test strip allows the user to test the blood glucose level only once, while a multi-use test strip, having multiple reaction zones on a single test strip, allows the user to perform multiple tests on a single test strips.

The term "non-destructive testing" refers to conducting a test on an object without materially changing the object's properties of interest. For example, after conducting a non-destructive testing on the enzyme reagent of a test strip, the enzyme reagent may still react with a blood sample and provide an accurate blood glucose reading.

According to an embodiment of the present invention, before conducting a quality assurance test with an inspection electric potential on a biosensor test strip, a homogenizing process may first be applied to the test strip to homogenize certain electrochemical characteristics on the surface of the conductor tracks of the test strip. Once homogenized, a quality assurance test with an inspection electric potential may be conducted on the test strip to determine whether the test strip is defective. Finally, the test strip may be subject to a reverse electric potential to substantially restore the test strip back to its original condition before the quality assurance test with an inspection electric potential.

For example, to homogenize the quality of a test trip, a cyclic oxidative and reductive electric potential may initially be applied across the enzyme reagent over the reaction zone to homogenize its electrochemical characteristic. The enzyme reagent may be placed between a part of the working electrodes and a part of the reference electrodes, and may cover a part of the working electrodes and a part of the reference electrodes. The cyclic oxidative and reductive electric potential may be applied to the enzyme reagent through the working electrode and the reference electrode.

Once the electrochemical characteristic of the test strip is homogenized, the electrical resistance of the enzyme reagent may be measured by applying a small inspection electric potential across the working and reference electrodes. The small inspection electric potential may be applied at two inspection pads, one electrically and very closely connected to the working electrode and the other one electrically and very closely connected to the reference electrode. The inspection electric potential may be kept small to prevent it from substantially altering the electrochemical characteristic of the enzyme reagent. Preferably, the inspection electric potential is 0.35 V or less. However, the exact inspection electric potential to be applied depends at least on the materials employed by the test strip, the material of the electrodes, and the enzyme reagent. A person of ordinary skill in the art would recognize that the present invention also applies to other types of electrodes, enzyme reagents, and test strips. The scope of the present invention is not limited by the inspection electric potential to be applied.

As previously described, the small inspection electric potential may be applied at two inspection pads respectively, electrically connected to the working electrode and reference electrode respectively. Alternatively, an inspection pad may be located on the working electrode or the reference electrode. It should be noted that the measured resistance across the two inspection pads may depend on the inherent electrical resistance of the conductor between the inspection pads and the electrodes. The electrical resistance of the conductor tends to vary depending on the manufacturing process or on other factors. Accordingly, the inspection pads may preferably be placed near the working and reference electrodes, preferably less than 1 centimeter. In addition, to prevent the enzyme reagent from degrading during the inspection, the small voltage may preferably be applied only for a very short period of time.

Once the electrical resistance is measured, whether the electrical resistance is within an acceptable range may be determined. If not, the defective test strip may be identified or marked.

Embodiments of the present invention provide non-destructive means to determine the electrochemical characteristics in biosensor test strips. After the inspection electric potential is applied, a reverse electric potential may be applied within a short period of time at the inspection pads to substantially eliminate degradation of the enzyme reagent caused by the inspection electric potential. According to an embodiment of the present invention, the reverse electric potential may be the opposite of the inspection electric potential between the inspection pads. For example, if the inspection electric potential is +0.35 V, the reverse electric potential may be −0.35 V. In addition, the duration of the reverse electric potential may be substantially the same as the duration of the inspection electric potential. Thus, by applying a reverse electric potential for the same short period of time, one may substantially prevent the potassium ferricyanide in the enzyme reagent from degradation. According to an embodiment of the present invention, the inspection electric potential, and the reverse electric potential may be a fixed electric potential, or a variable electric potential.

As previously mentioned, the inspection electric potential to be applied depends on the conductive material used for the electrodes and their associated layouts. For example, if the conductive material is copper foil with gold plating, applying an inspection electric potential of 0.35 V or less for 5 seconds or less (or 0.05 V or less for 0.1 second or less), and applying an opposite reverse electric potential for the same time interval would not cause the potassium ferricyanide in the enzyme reagent to degrade, thereby maintaining its electrochemical characteristics. Similarly, if the conductive material is silver paste or carbon paste, applying an inspection electric potential of 0.35 V or less for 5 seconds or less (or 0.15 V or less for 0.1 second or less), and applying an opposite reverse electric potential for the same time interval would not cause the potassium ferricyanide in the enzyme reagent to degrade, thereby maintaining its electrochemical characteristics.

According to an embodiment of the present invention, the enzyme reagent may comprise glucose oxidase (GOD), glucose dehydrogenase (GDH), and/or potassium ferricyanide. In addition, the enzyme reagent may further comprise citric acid, phosphoric acid, nonionic surfactant, deionized water and/or carbon nanotube. However, the specific composition of the enzyme reagent is not material to the present invention. Instead, a person of ordinary skill in the art would recognize that the present invention is applicable to other kinds of enzyme reagent.

FIG. 1 is a diagram illustrating a cyclic oxidative and reductive electric potential according to an embodiment of the present invention. According to an embodiment of the present invention, the cyclic oxidative and reductive electric potential is a cyclic electric potential cyclically varying between a positive voltage and the negative voltage. The cyclic electric potential may begin with a zero voltage. The cyclic electric potential may then be increased from the zero voltage to a positive voltage (+0.45V), decreased to a negative voltage (−0.45V), and finally back to the zero voltage, thereby completing a cycle (a zero-positive-zero-negative-zero cycle). Alternatively, the cyclic electric potential may be decreased from the zero voltage to a negative voltage (−0.45V), increased to a positive voltage (0.45V), and finally back to the zero voltage, thereby completing a cycle (a zero-negative-zero-positive-zero cycle). It should be noted that the cycle may also begin with a positive voltage, such as a positive-zero-negative-zero-positive cycle, or may begin with a negative voltage, such as a negative-zero-positive-zero-negative cycle.

As shown in FIG. 1, the voltage-current relationship of the enzyme reagent tends to stabilize after the first cyclic oxidative and reductive electric potential. As illustrated, for the given voltage of −0.2 V, the corresponding current value at point 1 for the first cycle is approximately 0.4 e-5 A, and the corresponding current values at point 2 for the second cycle and point 3 for the third cycle are approximately 0.6 e-5 A. In fact, the voltage-current relationship curves tend to be the same as the number of cycle increases, typically after the first cycle. After the cyclic oxidative and reductive electric potential treatment, the electrochemical characteristics of the test strip are stabilized or homogenized, and may now provide a more accurate electrical resistance when the inspection electric potential is applied.

Figure 2:
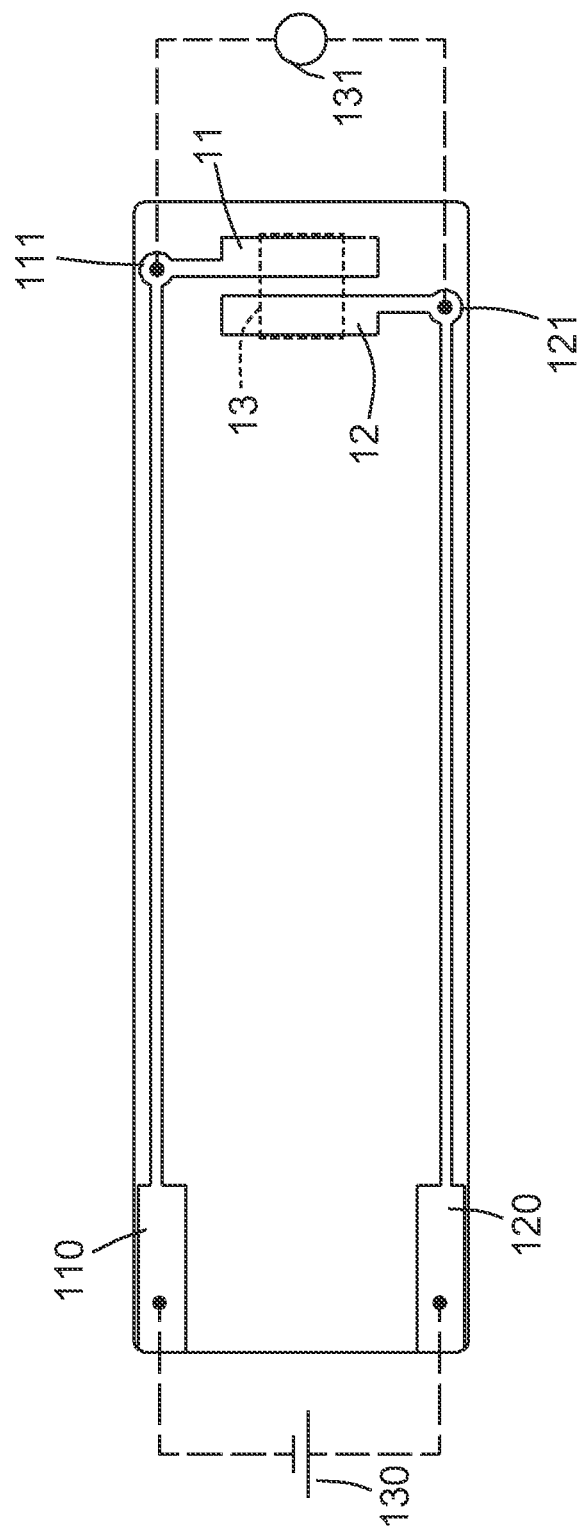
FIG. 2 is a simplified top plan view of a test strip and associated testing methods according to embodiments of the present invention.

FIG. 2 is a simplified top plan view of a test strip 200 and its testing method according to embodiments of the present invention. As shown, the enzyme reagent 13 is placed between, and covers part of, the working electrode 11 and the reference electrode 12. The working electrode 11 is electrically connected to the first inspection pad 111 and electrically connected to the first contact pad 110. The reference electrode 12 is electrically connected to the second inspection pad 121 and electrically connected to the second contact pad 120.

According to an embodiment of the present invention, the enzyme reagent 13 is first subject to a cyclic oxidative and reductive electric potential to homogenize its electrochemical characteristic. This can be accomplished by applying a cyclic electric potential to the first contact pad 110 and the second contact pad 120 by using the homogenizing device 130, thereby causing the cyclic oxidative and reductive electric potential to pass through the enzyme reagent 13. A person of ordinary skill in the art would recognize that there are many ways to perform this step, and the scope of the present invention is not limited to the exact method used for subjecting the enzyme reagent 13 to a homogenized condition. For example, a person of ordinary skill in the art would recognize that the cyclic electric potential may also be applied to the first inspection pad 111 and the second inspection pad 121 through the electronic device 131.

Once the electrochemical characteristic of the enzyme reagent 13 is homogenized, the electrical resistance of the enzyme reagent 13 may be measured by the electronic device 131, which applies a small inspection electric potential at the first inspection pad 111 and the second inspection pad 121. Preferably, the inspection electric potential is 0.35 V or less. As previously mentioned, to obtain a more accurate reading of the electrical resistance, the first inspection pad 111 shall be close to the working electrode 11, and the second inspection pad 121 shall be close to the reference electrode 12, preferably less than 1 centimeter. Thereafter, the electronic device 131 may apply a reverse electric potential at the first inspection pad 111 and the second inspection pad 121 to substantially restore the enzyme reagent 13 to its original condition before the inspection electric potential is applied. Once the electrical resistance of the enzyme reagent 13 is measured by the electronic device 131, the electrochemical characteristics of the test strip 200 may be determined.

Figure 3:
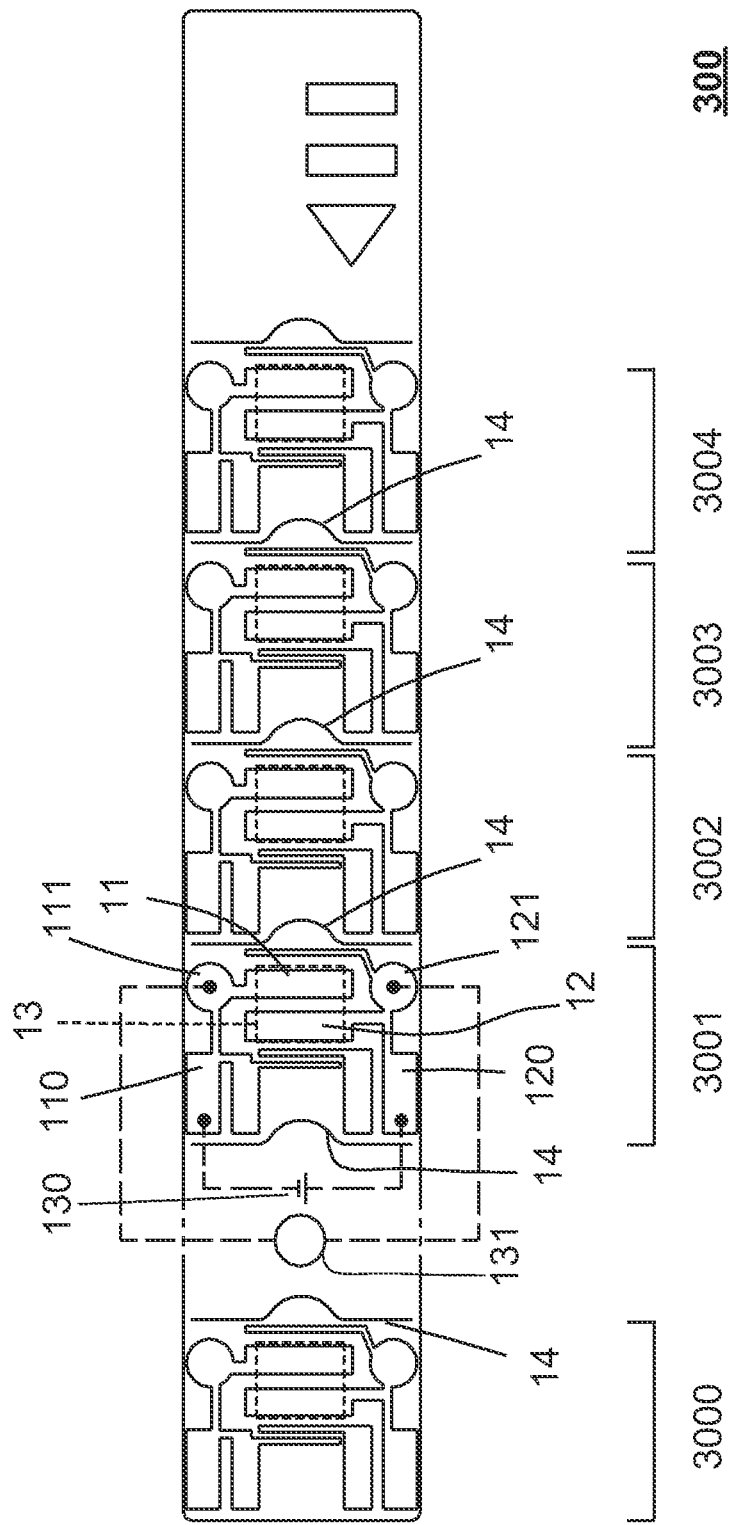
FIG. 3 is a simplified top plan view of a test strip and associated testing methods according to embodiments of the present invention.

FIG. 3 is a simplified top plan view of the test strip 300 and associated testing methods according to embodiments of the present invention. The test strip 300 is a multi-use test strip, which comprises multiple test sections, each being capable of working with a blood glucose meter to obtain the blood glucose level. As shown, the test sections 3000, 3001, 3002, 3003 and 3004 are located on the same test strip 300. A test section may be removed from the test strip 300 by bending along its associated pre-break line 14.

Because each of the test sections will be used to provide a blood glucose reading, a quality assurance test with an inspection electric potential may be performed on each of them. For example, regarding the test section 3001, the electrochemical characteristic of its enzyme reagent 13 on the working electrode 11 and the reference electrode 12 may be homogenized by the homogenizing device 130, which may apply a cyclic electric potential to the first inspection pad 111 and the second inspection pad 121. Then, the electronic device 131 may apply a small inspection electric potential to measure the electrical resistance between the first inspection pad 111 and the second inspection pad 121, and then may apply a reverse electric potential to restore the enzyme reagent 13. With the electrical resistance of the enzyme reagent 13 measured, the electrochemical characteristics of the test section 3001 may be determined.

Figure 4:
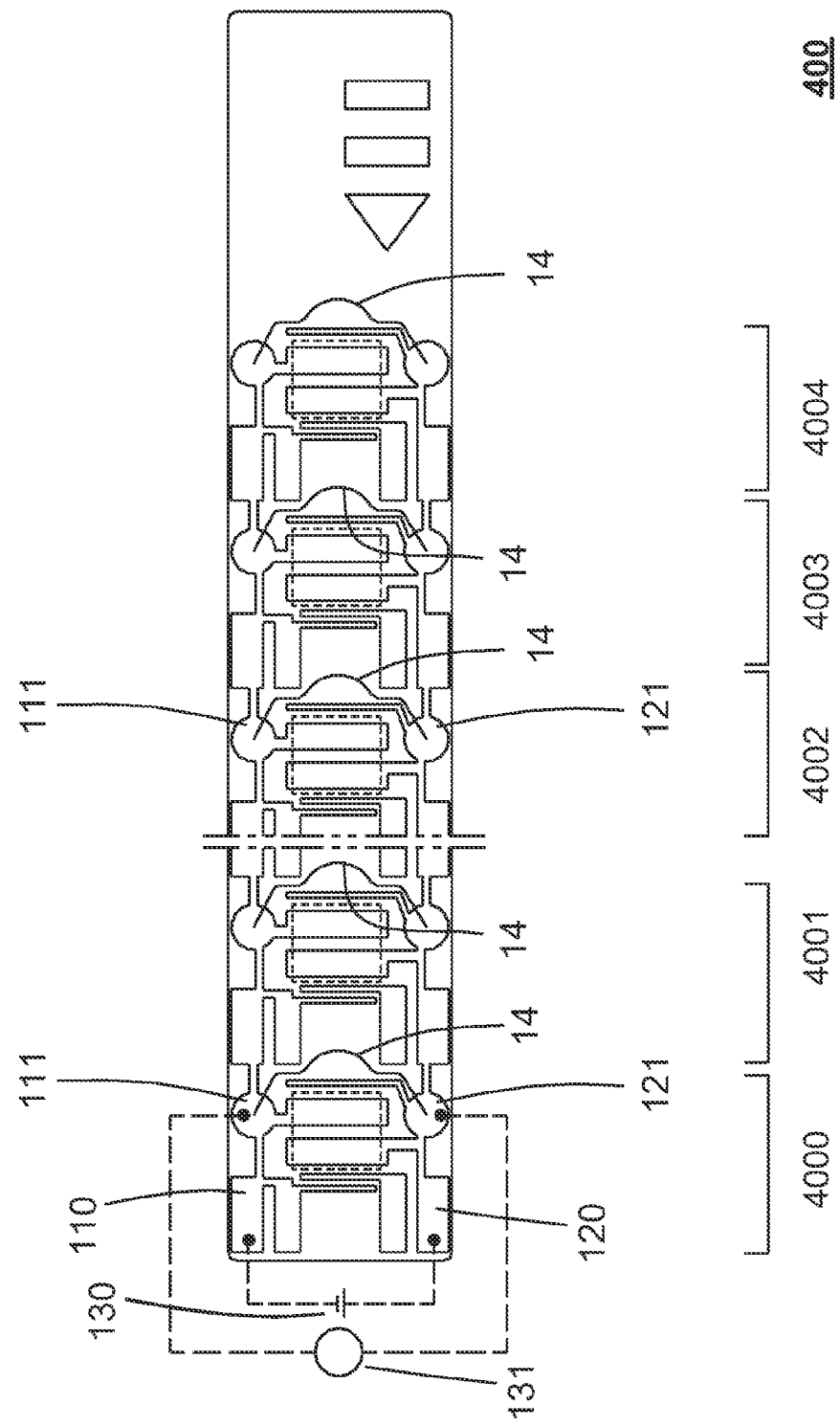
FIG. 4 is a simplified top plan view of a test strip and associated testing methods according to embodiments of the present invention.

FIG. 4 is a simplified top plan view of the test strip 400 and associated testing methods according to embodiments of the present invention, wherein all the test sections are electrically connected and wherein the pre-break lines 141 are slightly different from the pre-break lines depicted in FIG. 3. As shown, the test strip 400 may comprise, but not limited to, test sections 4000, 4001, 4002, 4003 and 4004. A test section may be removed from the test strip 400 by bending along its associated pre-break line 14. Moreover, the working electrode 11 and the first contact pad 110 of each test section may be connected in series, and the reference electrode 12 and the second contact pad 120 of each test section may be connected in series. For example, the first inspection pad 111 of the test section 4002 is electrically connected to the first inspection pad 111 and the first contact pad 110 of the test section 4000. Similarly, the second inspection pad 121 of the test section 4002 is electrically connected to the second inspection pad 121 and the second contact pad 120 of the test section 4000. Through serial connections, the homogenizing device 130 may apply the cyclic oxidative and reductive electric potential throughout each of the test sections. In addition, an inspection electric potential may be applied on the first inspection pad 111 and the second inspection pad 121, and the electronic device 131 may then measure the electrical resistance of the enzyme reagent at each of the test sections to assure its homogeneous quality. Finally, a reverse electric potential may be applied to each of the test sections to restore it to its original condition before inspection electric potential is applied.

Figure 5:
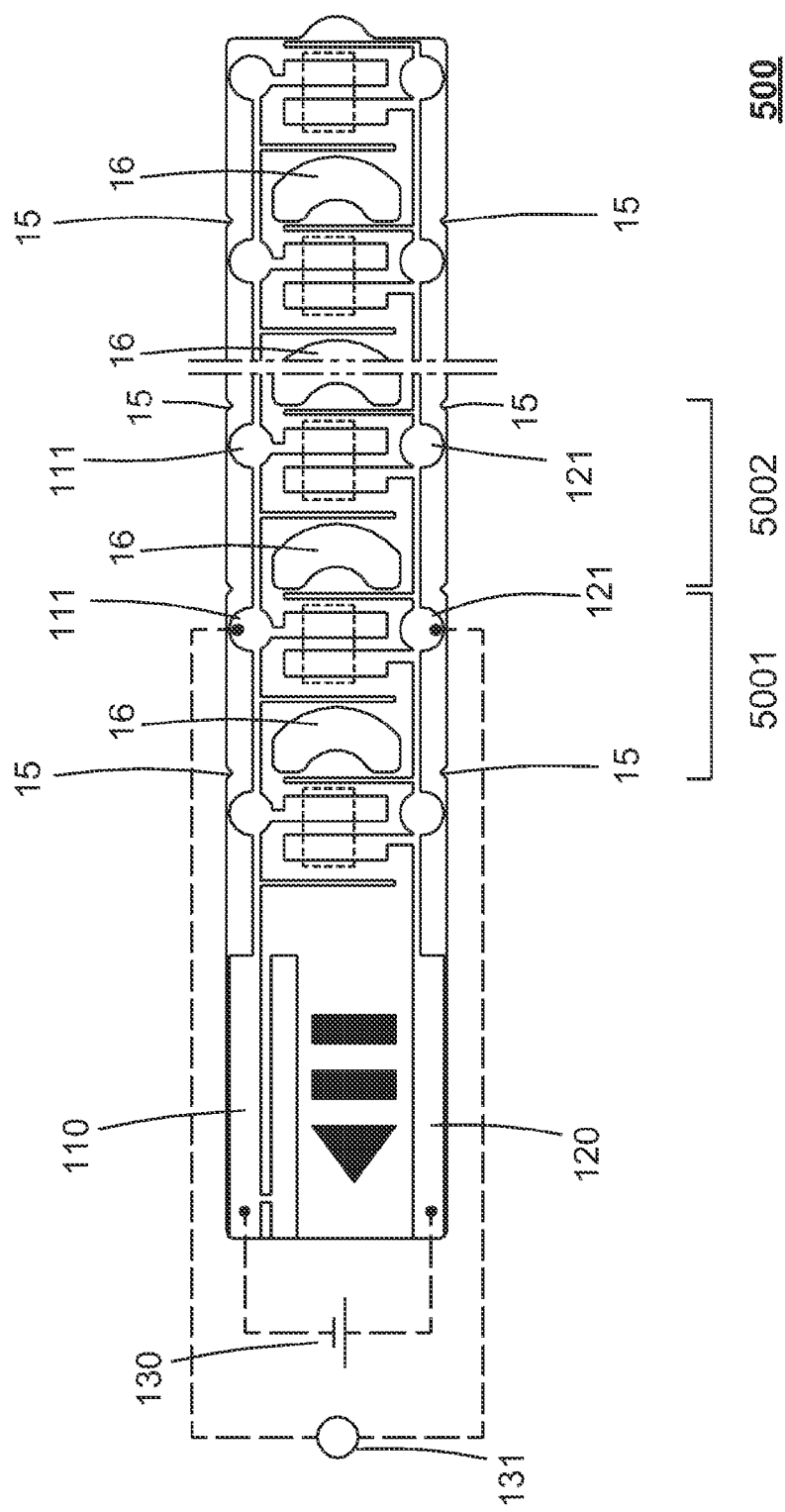
FIG. 5 is a simplified top plan view of a test strip and associated testing methods according to embodiments of the present invention.

FIG. 5 is a simplified top plan view of the test strip 500 and associated testing methods according to embodiments of the present invention. As shown, the test strip 500 may comprise, but not limited to, test sections 5001 and 5002. A test section may be removed from the test strip 500, in part, by bending along its associated pre-cut notches 15 and pre-formed holes 16. Moreover, each of the test sections may share the same first contact pad 110 and the second contact pad 120. For example, the first inspection pad 111 of the test section 5002 is electrically connected to the first inspection pad 111 of the test section 5001 and the first contact pad 110. Similarly, the inspection pad 121 of the test section 5002 is electrically connected to the inspection pad 121 of the test section 5001 and the second contact pad 120. Through such connections, the homogenizing device 130 may apply the cyclic oxidative and reductive electric potential throughout each of the test sections. In addition, an inspection electric potential may be applied on the first inspection pad 111 and the second inspection pad 121, and the electronic device 131 may then measure the electrical resistance of the enzyme reagent at each of the test sections to assure its homogeneous quality. Finally, a reverse electric potential may be applied to each of the test sections on the first inspection pad 111 and the second inspection pad 121 to restore to the original condition before the inspection electric potential is applied.

What is claimed is:

1. A method for determining an electrochemical characteristic associated with a test strip, comprising:
    applying a cyclic electric potential to the test strip to stabilize the electrochemical characteristic of an enzyme reagent on the test strip;
    conducting a quality assurance test with an inspection electric potential on the test strip; and
    subjecting the test strip to a reverse electric potential adapted to substantially restore the test strip back to an original condition before the inspection electric potential is applied.

2. The method of claim 1, wherein the test strip comprises a working electrode, a reference electrode and an enzyme reagent placed on the working electrode and the reference electrode.

3. The method of claim 2, wherein the working electrode is electrically connected to a first inspection pad, and the reference electrode is electrically connected to a second inspection pad.

4. The method of claim 3, wherein a distance between the working electrode and the first inspection pad is less than 2 centimeters, and a distance between the reference electrode and the second inspection pad is less than 2 centimeters.

5. The method of claim 3, wherein the enzyme reagent comprises potassium ferricyanide.

6. The method of claim 5, wherein the enzyme reagent further comprises glucose oxidase (GOD), glucose dehydrogenase (GDH), citric acid, phosphoric acid, nonionic surfactant, and deionized water.

7. The method of claim 5, wherein the cyclic electric potential has a cycle which is selected from a group consisting of a positive-zero-negative-zero-positive cycle beginning with a positive voltage, a zero-positive-zero-negative-zero cycle beginning with a zero voltage, a zero-negative-zero-positive-zero cycle beginning with a zero voltage, and a negative-zero-positive-zero-negative cycle beginning with a negative voltage.

8. The method of claim 3, wherein the quality assurance test with an inspection electric potential comprises applying an inspection electric potential between the first inspection pad and the second inspection pad for a first time interval to measure electrical resistance associated with the enzyme reagent on the working electrode and the reference electrode.

9. The method of claim 8, wherein said subjecting the test strip to the reverse electric potential comprises applying the reverse electric potential that is opposite to the inspection electric potential between the first inspection pad and the second inspection pad for a second time interval.

10. The method of claim 9, wherein the first time interval and the second time interval required to apply the inspection electric potential and the reverse electric potential are substantially the same.

11. The method of claim 9, wherein the reverse electric potential and the second time interval are adapted to prevent potassium ferricyanide in the enzyme reagent from degradation.

12. The method of claim 11, wherein the first contact pad, the first inspection pad, the working electrode, the second contact pad, the second inspection pad and the reference electrode comprise copper foil with gold plating, and the inspection electric potential is less than 0.35 volt and the first time interval is less than 5 seconds.

13. The method of claim 11, wherein the first contact pad, the first inspection pad, the working electrode, the second contact pad, the second inspection pad and the reference electrode comprise silver paste, and the inspection electric potential is less than 0.35 volt and the first time interval is less than 5 seconds.

14. The method of claim 11, wherein the first contact pad, the first inspection pad, the working electrode, the second contact pad, the second inspection pad and the reference electrode comprise carbon paste, and the inspection electric potential is less than 0.35 volt and the first time interval is less than 5 seconds.

15. A method for determining an electrochemical characteristic associated with a first test section of a test strip, comprising:
    applying a cyclic electric potential to the first test section of the test strip to stabilize the electrochemical characteristic of an enzyme reagent on the test strip;
    conducting a quality assurance test with an inspection electric potential on the first test section; and
    subjecting the first test section to a reverse electric potential adapted to substantially restore the first test section back to an original condition before the inspection electric potential is applied,
    wherein the test strip further comprises a second test section, and the first test section can be separated from the test strip through an associated pre-break line.

16. The method of claim 15, wherein the first test section comprises a first working electrode and a first reference electrode, the second test section comprises a second working electrode and a second reference electrode, and the first working electrode is electrically connected to the second working electrode and the first reference electrode is electrically connected to the second reference electrode.

17. A test strip comprising at least one test section for measuring blood glucose in a blood sample, the test section comprising:
    a working electrode;
    a reference electrode;
    an enzyme reagent placed between the working electrode and the reference electrode;
    a first inspection pad electrically connected to the working electrode;
    a second inspection pad electrically connected to the reference electrode;
    a first contact pad electrically connected to the working electrode; and
    a second contact pad electrically connected to the reference electrode,
    wherein the first contact pad and the second contact pad are applied with a cyclic electric potential to stabilize an electrochemical characteristic of an enzyme reagent on the test strip, and the first inspection pad and the second inspection pad are applied with an inspection electric potential to measure an electrical resistance of the enzyme reagent, the test strip comprises more than one test sections, the first inspection pads of the different test sections are electrically connected with each other, and the second inspection pads of the different test sections are electrically connected with each other.

18. The test strip of claim 17, wherein the test sections share a same first contact pad and a same second contact pad.

* * * * *